(12) United States Patent
Takeuchi et al.

(10) Patent No.: US 10,361,107 B2
(45) Date of Patent: Jul. 23, 2019

(54) CONTENT MOVING DEVICE

(71) Applicant: SINFONIA TECHNOLOGY CO., LTD., Minato-ku (JP)

(72) Inventors: Haruki Takeuchi, Minato-ku (JP); Kazuhiro Tsuji, Minato-ku (JP); Minetaka Maeda, Minato-ku (JP)

(73) Assignee: SINFONIA TECHNOLOGY CO., LTD., Minato-ku (JP)

( * ) Notice: Subject to any disclaimer, the term of this patent is extended or adjusted under 35 U.S.C. 154(b) by 24 days.

(21) Appl. No.: 15/738,027

(22) PCT Filed: Jun. 8, 2016

(86) PCT No.: PCT/JP2016/067033
§ 371 (c)(1),
(2) Date: Dec. 19, 2017

(87) PCT Pub. No.: WO2016/204036
PCT Pub. Date: Dec. 22, 2016

(65) Prior Publication Data
US 2018/0308731 A1    Oct. 25, 2018

(30) Foreign Application Priority Data
Jun. 19, 2015 (JP) .................... 2015-124064

(51) Int. Cl.
| H01L 21/677 | (2006.01) |
| H01L 21/673 | (2006.01) |
| A61L 2/20 | (2006.01) |

(52) U.S. Cl.
CPC .......... *H01L 21/67373* (2013.01); *A61L 2/20* (2013.01); *H01L 21/677* (2013.01);
(Continued)

(58) Field of Classification Search
CPC .......... H01L 21/67775; H01L 21/67373; H01L 21/67376; H01L 21/67379; H01L 21/67772
See application file for complete search history.

(56) References Cited

U.S. PATENT DOCUMENTS

| 5,788,458 A | * | 8/1998 | Bonora ............. H01L 21/67772 414/416.01 |
| 6,152,669 A | * | 11/2000 | Morita .............. H01L 21/67772 414/217 |
| 8,550,006 B2 | * | 10/2013 | Wada ................ H01L 21/67775 104/89 |

FOREIGN PATENT DOCUMENTS

| JP | 5-82624 A | 4/1993 |
| JP | 7-66274 A | 3/1995 |
| JP | 7-297257 A | 11/1995 |

OTHER PUBLICATIONS

International Search Report dated Aug. 23, 2016, in PCT/JP2016/067033 filed Jun. 8, 2016.

* cited by examiner

*Primary Examiner* — Jonathan Snelting
(74) *Attorney, Agent, or Firm* — Oblon, McClelland, Maier & Neustadt, L.L.P.

(57) ABSTRACT

Reliability in the restriction of the movement of a container is improved.
A content moving device 1 includes: a table portion 20 on which a container 50 is placed; and a restricting mechanism 30. A flange 55 of the container 50 is shaped to provide a recessed portion 56a. A restricting mechanism 30 includes: a collar portion 31; a first restricting portion 32 configured to be located in the recessed portion 56a; a second restricting portion 33a provided above the first restricting portion 32 and inward of the collar portion 31; and a second moving mechanism. The second moving mechanism is configured to (Continued)

move the second restricting portion 33a along an extending direction B between a first position, in which the second restricting portion 33a is opposed to the flange 55 of the container 50 in an up-down direction A, and a second position, in which the second restricting portion 33a is opposed to the recessed portion 56a in the up-down direction A without being opposed to the flange 55 in the up-down direction A.

7 Claims, 9 Drawing Sheets

(52) U.S. Cl.
CPC .. *H01L 21/67376* (2013.01); *H01L 21/67379* (2013.01); *H01L 21/67772* (2013.01)

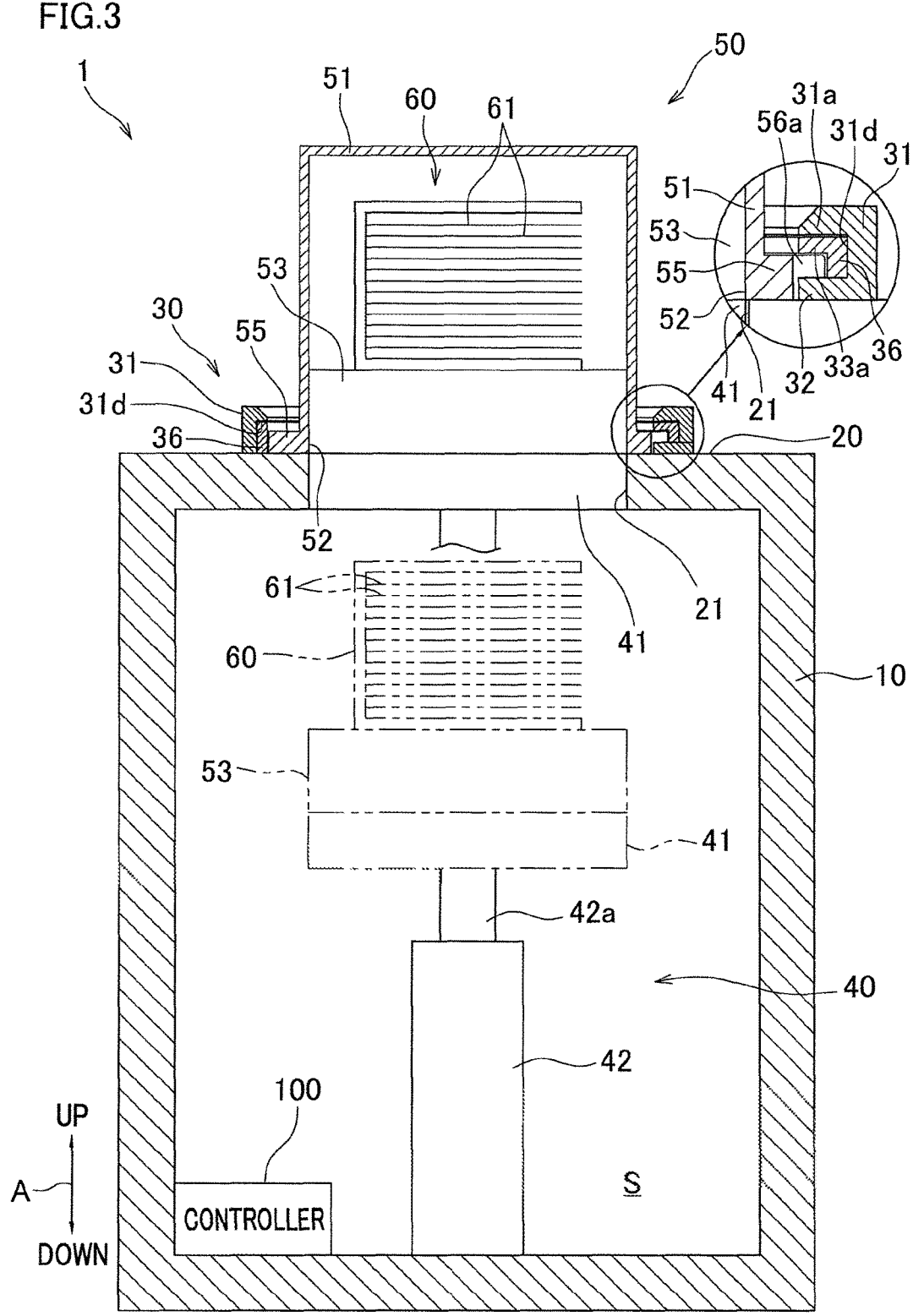

CONTENT MOVING DEVICE

TECHNICAL FIELD

The present invention relates to a content moving device configured to move content contained in a container to an internal space.

BACKGROUND ART

Patent Literature 1 describes the following technique: when a container, in which content such as semiconductor wafers is contained, is placed on a table portion of a main body case, an automatic lock mechanism is actuated, to restrict the movement of the container by holding down a flange of a container main body from above.

CITATION LIST

Patent Literature

Patent Literature 1: Japanese Unexamined Patent Publication No. H07-66274

SUMMARY OF INVENTION

Technical Problem

In the above technique described in Patent Literature 1, the automatic lock mechanism holds down the flange of the container main body from above. It can be considered that the automatic lock mechanism includes a restricting portion configured to restrict the movement of the container main body, and the restricting portion is configured to rotate from the outside of the flange, for example, so as to hold the flange from above. In such a configuration, in which the automatic lock mechanism rotates the restricting portion to hold down the flange from above, foreign matter, for example, may be caught between the flange and the restricting portion if it exists on the flange. As a result, the automatic lock mechanism cannot restrict the movement of the container, disadvantageously.

In view of the above, an object of the present invention is to provide a content moving device with improved reliability in the restriction of the movement of a container.

Solution to Problem

According to an embodiment of the present invention, a content moving device is configured to allow a container to be placed thereon, the container including: a container main body capable of containing content and having an opening which opens downward; a bottom lid capable of hermetically closing the opening; and a flange provided around the opening and shaped to provide at least one recessed portion. The content moving device includes: a main body case having an internal space; a table portion provided on an upper wall of the main body case and configured to allow the container to be hermetically placed on the table portion; a restricting mechanism configured to restrict movement of the container placed on the table portion; and a first moving mechanism configured to move the content to the internal space with the bottom lid of the container restricted by the restricting mechanism. The restricting mechanism includes: a collar portion provided on the table portion in a standing manner and configured to surround the flange of the container placed on the table portion; a first restricting portion provided inward of the collar portion and configured to be located in the recessed portion when the container is placed on the table portion; at least one second restricting portion shorter than the recessed portion with respect to an extending direction of the flange in which the flange extends, the second restricting portion being provided above the first restricting portion and inward of the collar portion; and a second moving mechanism configured to move the second restricting portion along the extending direction between a first position, in which the second restricting portion is opposed to the flange of the container placed on the table portion in an up-down direction, and a second position, in which the second restricting portion is opposed to the recessed portion in the up-down direction without being opposed to the flange in the up-down direction.

In the above arrangement, moving the second restricting portion from the second position to the first position causes the second restricting portion to be opposed to the flange in the up-down direction, and this restricts the movement of the container placed on the table portion in the up-down direction. If foreign matter exists on the flange of the container and within the moving range of the second restricting portion when restricting the movement of the container placed on the table portion as above, the second restricting portion moves along the extending direction of the flange, and therefore the second restricting portion pushes the foreign matter aside to move from the second position to the first position. This reduces the possibility that foreign matter is caught between the second restricting portion and the flange, and makes it easier to restrict the movement of the container in the up-down direction. As a result, reliability in the restriction of the movement of the container is improved. Furthermore, because the first restricting portion is provided, the movement of the container is restricted with respect to the extending direction of the flange, and foreign matter is less likely to enter the recessed portion of the container placed on the table portion.

In the above aspect of the present invention, it is preferable that a length of the second restricting portion in the extending direction is equal to or shorter than that of the first restricting portion, and an entirety of the second restricting portion is opposed to the first restricting portion in the up-down direction when the second restricting portion is in the second position. This further reduces the range of the movement of the container with respect to the extending direction of the flange.

In the above aspect of the present invention, it is preferable that when the second restricting portion is in the first position, a first end of the second restricting portion in the extending direction is opposed to the flange in the up-down direction and a second end of the second restricting portion in the extending direction is opposed to the first restricting portion in the up-down direction. Even if a gap exists between an end of the first restricting portion in the extending direction and the recessed portion when restricting the movement of the container placed on the table portion, foreign matter is less likely to enter the gap. This makes it easier to move the second restricting portion from the first position to the second position. This improves reliability in lifting the movement restriction of the container placed on the table portion.

In the above aspect of the present invention, it is preferable that the restricting mechanism further includes at least one opposed portion provided above the second restricting portion so as to protrude inward from the collar portion, the opposed portion being configured to be opposed to the second restricting portion in the up-down direction when the second restricting portion is in the second position. This reduces the possibility that a finger of a user or the like contacts the second restricting portion when the second restricting portion is moved.

In the above aspect of the present invention, it is preferable that the restricting mechanism includes a plurality of the second restricting portions provided apart from one another along the extending direction and respectively corresponding to a plurality of the recessed portions. This makes it possible to more effectively restrict the movement of the container placed on the table portion with respect to the up-down direction.

In the above aspect of the present invention, it is preferable that the restricting mechanism includes a plurality of the opposed portions configured to be respectively opposed to the second restricting portions in the up-down direction. This further reduces the possibility that a finger of a user or the like contacts the second restricting portion when the second restricting portions are moved.

Furthermore, in the above aspect of the present invention, it is preferable that the collar portion has an annular shape, and the second moving mechanism includes: a driving source; an annular portion provided inward of the collar portion and provided with the second restricting portions on an inner circumferential surface of the annular portion; and a transmission mechanism configured to transmit driving force from the driving source to the annular portion so as to rotate the annular portion. This makes it possible to move the second restricting portions by the single driving source while achieving simplification of the structure of the second moving mechanism.

Advantageous Effects of Invention

In the content moving device according to an embodiment of the present invention, moving the second restricting portion from the second position to the first position causes the second restricting portion to be opposed to the flange in the up-down direction, and this restricts the movement of the container placed on the table portion in the up-down direction. If foreign matter exists on the flange of the container and within the moving range of the second restricting portion when restricting the movement of the container placed on the table portion, the second restricting portion pushes the foreign matter aside to move from the second position to the first position. This reduces the possibility that foreign matter is caught between the second restricting portion and the flange, and makes it easier to restrict the movement of the container in the up-down direction. As a result, reliability in the restriction of the movement of the container is improved. Furthermore, because the first restricting portion is provided, the movement of the container is restricted with respect to the extending direction of the flange, and foreign matter is less likely to enter the recessed portion of the container placed on the table portion.

BRIEF DESCRIPTION OF THE DRAWINGS

FIG. 3 is a cross section taken along a line III-III in FIG. 2A.

DESCRIPTION OF EMBODIMENTS

The following will describe a content moving device according to an embodiment of the present invention, with reference to FIG. 1 to FIG. 7A and FIG. 7B.

Figure 1:
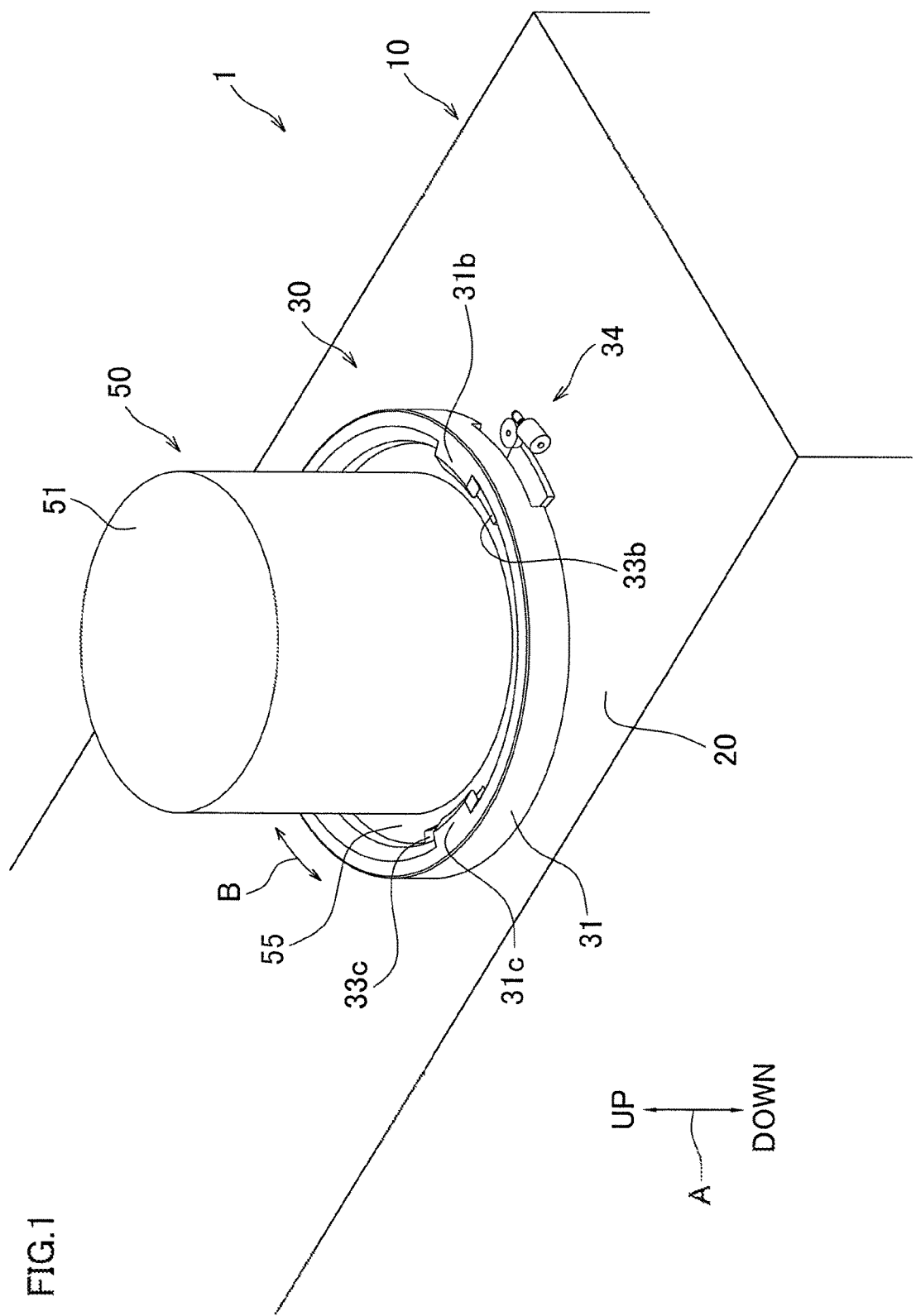
FIG. 1 is a perspective view of a main part of a content moving device related to an embodiment of the present invention.

As shown in FIG. 1 to FIG. 3, a content moving device 1 of the present embodiment includes: a main body case 10, a table portion 20, a restricting mechanism 30, and a first moving mechanism 40. The table portion 20 is configured to allow a container 50 to be placed thereon. The main body case 10 has a gas intake port and a discharge port (both of them are not illustrated). The gas intake port and the discharge port are connected to a gas generator via a hose (the gas generator and the hose are not illustrated). Hydrogen peroxide gas generated by the gas generator is introduced into an internal space S (see FIG. 3) of the main body case 10 through the gas intake port. Gas in the internal space S is discharged to the gas generator through the discharge port. In this way, the concentration of the hydrogen peroxide gas in the internal space S is adjusted. The content moving device 1 of the present embodiment functions as a sterilizer configured to sterilize content contained in the internal space S with hydrogen peroxide gas charged into the internal space S. Gas introduced from the gas generator may be sterilization gas other than hydrogen peroxide gas. The type of gas introduced into the internal space S may be changed, as needed, depending on the content contained in the internal space S.

As shown in FIG. 3, the container 50, which is configured to be placed on the content moving device 1 of the present embodiment, is capable of containing a cassette 60. The container 50 includes: a cylindrical container main body 51 having a closed upper end portion and an open bottom, and a bottom lid 53 capable of opening/closing an opening 52 provided at a bottom portion of the container main body 51. That is, the container 50 is a so-called bottom-opening container. The cassette 60 is a frame in which a plurality of slots (not illustrated) are provided in a vertically-stacked manner. Each slot is capable of containing a horizontally-oriented cell culture plate 61 for culturing cells. The cassette 60 is configured to hold cell culture plates 61 in parallel to each other, which are inserted into the respective slots. In regard to the content, only a single cell culture plate 61 may be contained, or an object other than the cell culture plate(s) 61 may be contained. The content contained in the cassette 60 is not particularly limited. For example, one or more semiconductor wafers may be contained in the cassette 60 and the cassette 60 may be contained in the container 50. In this case, gas suitable for the semiconductor wafers is charged into the internal space S by the gas generator.

As shown in FIG. 1 and FIG. 3, the main body case 10 has the internal space S, and has a substantially rectangular parallelepiped external shape. In the internal space S of the main body case 10, the first moving mechanism 40 and a controller 100 are provided. The controller 100 is configured to control the operation of the restricting mechanism 30, the first moving mechanism 40, and the like.

The table portion 20 is provided on an upper wall of the main body case 10. On the table portion 20, the container 50 is placed. A sealing member (not illustrated) is provided at a part of the table portion 20, the part being opposed to the flange 55 of the container 50. This allows the container 50 to be hermetically placed on the table portion 20 when the container 50 is placed on the table portion 20. As shown in FIG. 3, the table portion 20 has a communication hole 21. The communication hole 21 functions as a passage through which the bottom lid 53 of the container 50 and the cassette 60 (including the cell culture plates 61) are moved to the internal space S. The communication hole 21 has a circular shape with a diameter substantially equal to that of the opening 52 of the container 50.

The first moving mechanism 40 includes an up-down table 41 and an up-down mechanism 42. The first moving mechanism 40 is configured to move the cassette 60 to the internal space S together with the bottom lid 53 of the container 50 placed on the table portion 20. The up-down table 41 has a disc-like shape having a diameter slightly smaller than the diameter of the communication hole 21. A sealing member (not illustrated) is provided on an outer circumferential surface of the up-down table 41. This allows the up-down table 41 to hermetically close the communication hole 21 with respect to the internal space S. The up-down mechanism 42 in the present embodiment is formed by an air cylinder. The up-down mechanism 42 is configured to move the up-down table 41 between a closed position and an open position by extending/retracting a cylinder rod 42a. The closed position is indicated by a solid line in FIG. 3. In the closed position, the communication hole 21 is closed by the up-down table 41. The open position is indicated by a two-dot chain line in FIG. 3. In the open position, the bottom lid 53 of the container 50 and the cassette 60 (including wafers W) are located in the internal space S. The up-down mechanism 42 may have any structure as long as it is able to move the up-down table 41 to the closed position and to the open position.

As shown in FIG. 3, the bottom lid 53 of the container 50 has a top surface on which the cassette 60 is placed, and incorporates therein a locking/unlocking mechanism (not illustrated). The locking/unlocking mechanism has a structure substantially similar to that of the locking/unlocking mechanism described in Japanese Unexamined Patent Publication No. H07-66274. As shown in FIG. 4B, the locking/unlocking mechanism performs locking/unlocking by advancing/retracting each rod 53a, through an opening of a side wall of the bottom lid 53, with respect to a corresponding recess 51a provided at an inner circumferential surface of a lower end portion of the container main body 51. The up-down table 41 incorporates therein a camshaft and a camshaft driving mechanism, which are not illustrated. The camshaft protrudes upward from a central portion of an upper wall of the up-down table 41, and is configured to make spline engagement with a cam of the locking/unlocking mechanism when the bottom lid 53 is concentrically placed on the up-down table 41. The camshaft driving mechanism is configured to rotate the camshaft by a predetermined angle. The camshaft driving mechanism is configured to rotate the camshaft under the driving control of the controller 100, so as to cause the locking/unlocking mechanism to selectively take a locked state and an unlocked state. In the locked state, the bottom lid 53 hermetically seals off the inside of the container main body 51 to the outside air, by means of a sealing member (not illustrated) provided on an outer circumferential surface of the bottom lid 53.

Figure 4A:
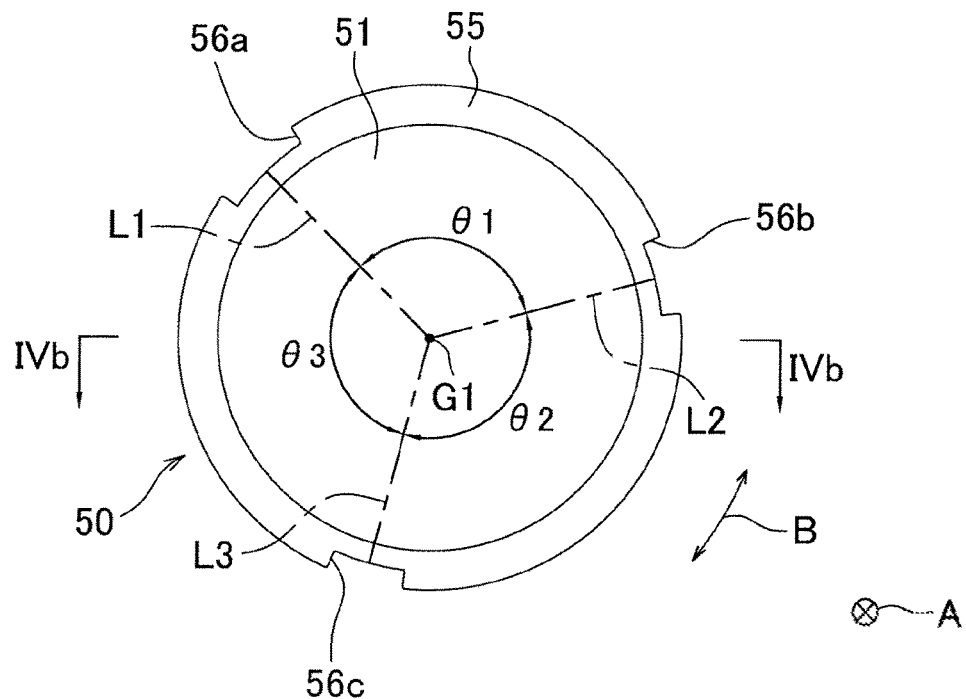
FIG. 4A is a plan view of the container shown in FIG. 1.
Figure 4B:
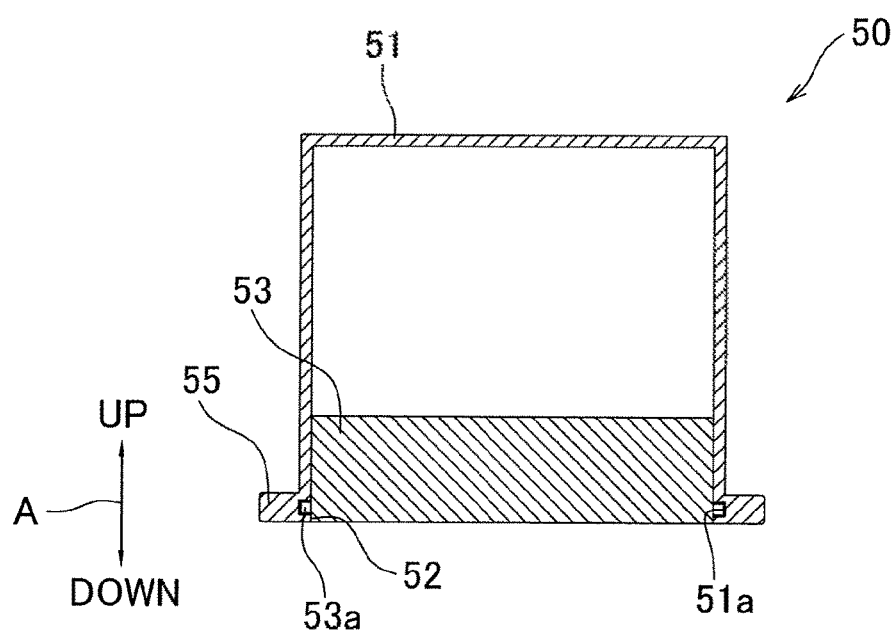
FIG. 4B is a cross section taken along a line IVb-IVb shown in FIG. 4A.

As shown in FIG. 4A and FIG. 4B, the container 50 has a flange 55 of an annular shape (circular ring shape) provided on an outer circumferential surface of the lower end portion of the container main body 51. That is, the flange 55 is provided around the opening 52. The flange 55 is shaped to provide three recessed portions 56a to 56c, each passing through the flange 55 in an up-down direction A. The length of the recessed portion 56a in an extending direction B is longer than that of the other recessed portions 56b and 56c. The extending direction B is the direction in which the flange 55 extends, and in this embodiment, the extending direction B is the rotational direction about a center G1 of the container 50. The two recessed portions 56b and 56c are shaped so as to have the substantially same length in the extending direction B of the flange 55. The three recessed portions 56a to 56c are arranged so as to be apart from one another in the extending direction B of the flange 55. Line segments connecting respective midpoints of the recessed portions 56a to 56c in the extending direction B of the flange 55 to the center G1 of the container 50 are called line segments L1 to L3. As shown in FIG. 4A, angles θ1 to θ3 formed by the line segments L1 to L3 are equal to one another.

Figure 5A:
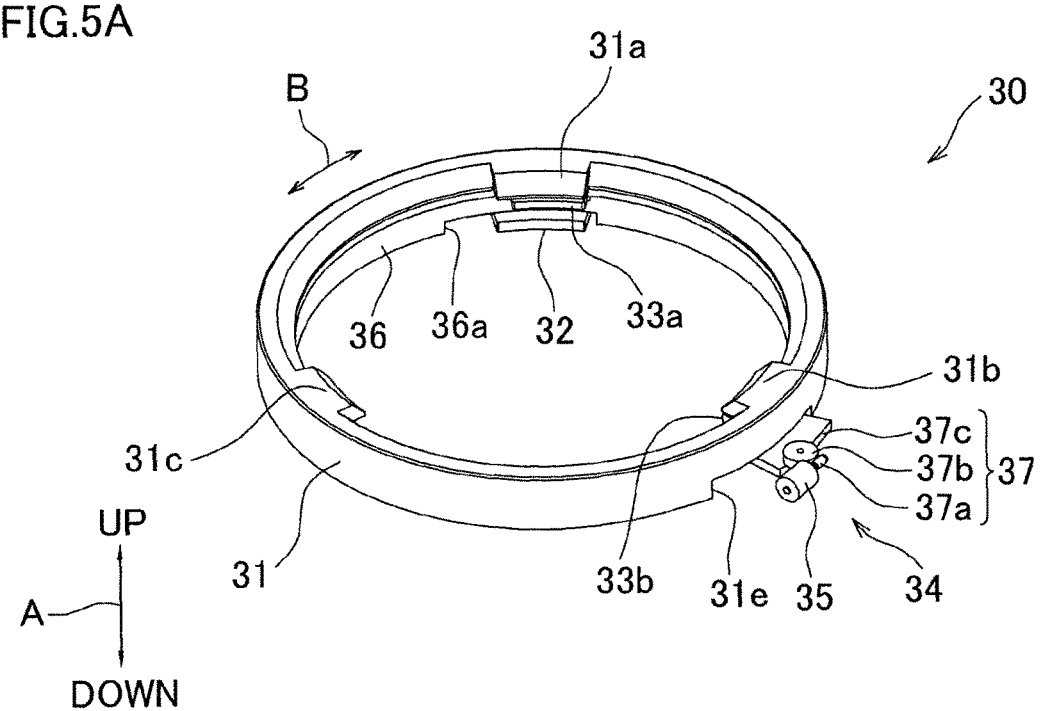
FIG. 5A is a perspective view of a restricting mechanism shown in FIG. 1, and illustrating the state in which second restricting portions are in their second position.
Figure 5B:
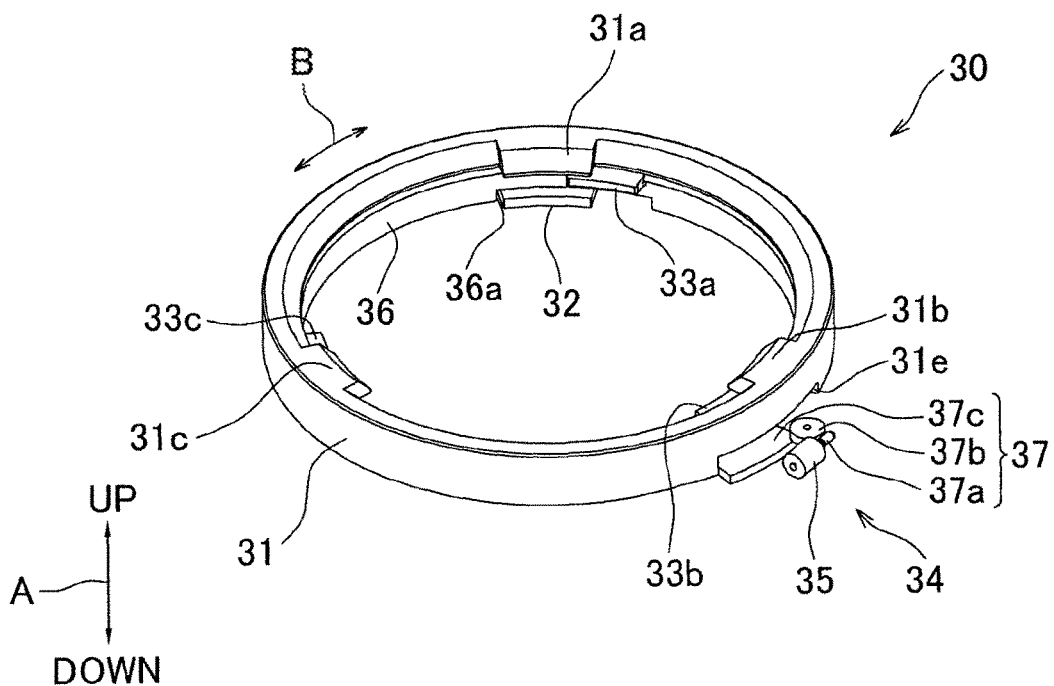
FIG. 5B is a perspective view of the restricting mechanism shown in FIG. 1, and illustrating the state in which the second restricting portions are in their first position.

As shown in FIG. 1, the restricting mechanism 30 is provided on the table portion 20, and around the container 50 placed on the table portion 20. The restricting mechanism 30 is configured to restrict horizontal and vertical movement of the container 50. As shown in FIG. 5A and FIG. 5B, the restricting mechanism 30 includes: a collar portion 31, a first restricting portion 32; three second restricting portions 33a to 33c; and a second moving mechanism 34. As shown in FIG. 1 and FIG. 3, the collar portion 31 is provided on the table portion 20 in a standing manner around the communication hole 21, so as to surround the flange 55 of the container 50 placed on the table portion 20. As shown in FIG. 2A, FIG. 2B, FIG. 5A, and FIG. 5B, the collar portion 31 has an annular shape (circular ring shape) so as to correspond to the flange 55. The inner diameter of the collar portion 31 is slightly larger than the outer diameter of the flange 55. The height of the collar portion 31 in the up-down direction A is larger than the thickness of the flange 55.

Figure 2A:
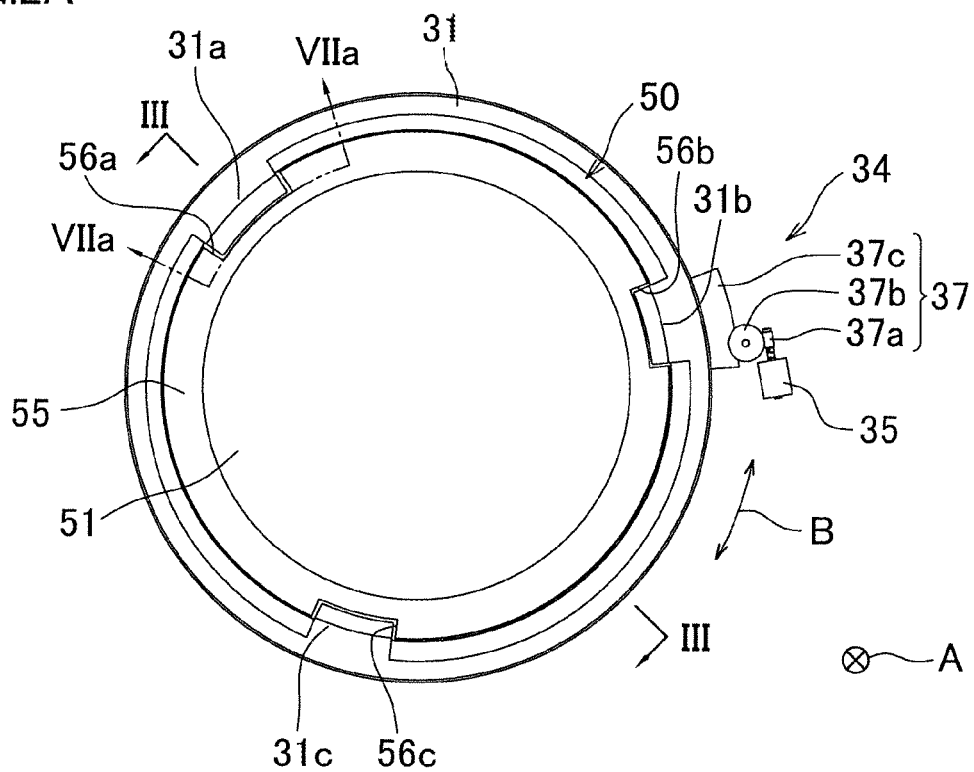
FIG. 2A is a plan view of the main part of the content moving device shown in FIG. 1, and illustrating the state in which the movement of a container is not restricted.
Figure 2B:
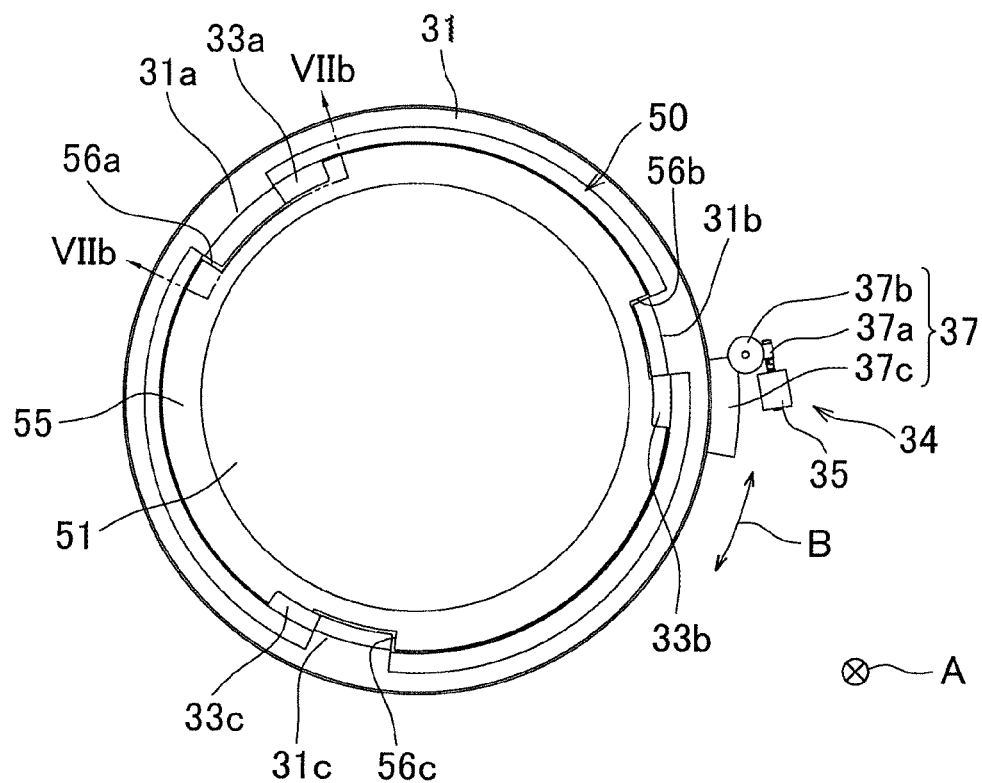
FIG. 2B is a plan view of the main part of the content moving device shown in FIG. 1, and illustrating the state in which the movement of the container is restricted.

On the collar portion 31, there are provided three opposed portions 31a to 31c respectively opposed to the three second restricting portions 33a to 33c in the up-down direction A. The three opposed portions 31a to 31c are provided above the second restricting portions 33a to 33c, so as to protrude inward from the collar portion 31. As shown in FIG. 2A and FIG. 2B, the three opposed portions 31a to 31c respectively pass through the three recessed portions 56a to 56c when the container 50 is placed on the table portion 20. The opposed portion 31a corresponds to the recessed portion 56a. The opposed portion 31b corresponds to the recessed portion 56b. The opposed portion 31c corresponds to the recessed portion 56c. That is, the three opposed portions 31a to 31c are arranged so as to be apart from one another in the extending direction B, correspondingly to the three recessed portions 56a to 56c. The opposed portion 31a is slightly shorter than the recessed portion 56a and longer than the two opposed portions 31b and 31c in the extending direction B. The two opposed portions 31b and 31c have the substantially same length in the extending direction B, which is slightly shorter than that of the recessed portions 56b and 56c. The above-described arrangement enables positioning of the container 50 with respect to the extending direction B when the container 50 is placed on the table portion 20. As shown in FIG. 3, the collar portion 31 has, on its inner circumferential surface, an annular groove 31d. The width of the groove 31d in the up-down direction A is larger than the thickness of the flange 55. As shown in FIG. 5A and FIG. 5B, the collar portion 31 is shaped to provide a recessed portion 31e passing through the collar portion 31 in its radial direction.

As shown in FIG. 3, FIG. 5A, and FIG. 5B, the first restricting portion 32 is provided so as to protrude inward from a portion of a lower end portion of the collar portion 31, the portion corresponding to the opposed portion 31a. The first restricting portion 32 is provided inward of the collar portion 31, and the entirety of the first restricting portion 32 is opposed to the opposed portion 31a. The first restricting portion 32 of the present embodiment is shaped so that its planar shape and planar size are substantially equal to those of the opposed portion 31a. However, the planar shape and planar size of the first restricting portion 32 may be different from those of the opposed portion 31a as long as the first restricting portion 32 corresponds to the recessed portion 56a. In other words, it is only required for the first restricting portion 32 to be shorter than the recessed portion 56a with respect to the extending direction B, so as to allow the first restricting portion 32 to be positioned in the recessed portion 56a when the container 50 is placed on the table portion 20. Because the first restricting portion 32 as described above is provided, it is possible to restrict the movement of the container 50 placed on the table portion 20 with respect to the extending direction B. Furthermore, because the flange 55 is surrounded by the collar portion 31, it is possible to restrict the movement of the container 50 placed on the table portion 20 with respect to horizontal directions other than the extending direction B. It should be noted that a restricting portion equivalent to the first restricting portion 32 may be provided so as to correspond to the opposed portion 31b, 31c.

The second moving mechanism 34 includes a drive motor 35, an annular portion 36, and a transmission mechanism 37. The transmission mechanism 37 includes: a worm gear 37a provided to a rotation shaft of the drive motor 35; a pinion gear 37b meshing with the worm gear 37a; and a rack gear 37c meshing with the pinion gear 37b. The rack gear 37c is provided on the table portion 20 so as to be movable within the recessed portion 31e along the extending direction B. The drive motor 35 is driven and controlled by the controller 100. As the drive motor 35 is driven, the rack gear 37c is moved along the extending direction B, via the worm gear 37a and the pinion gear 37b. The rack gear 37c is fixed to an outer circumferential surface of the annular portion 36. That is, as the rack gear 37c moves along the extending direction B, the annular portion 36 also rotates along the extending direction B.

Figure 6A:
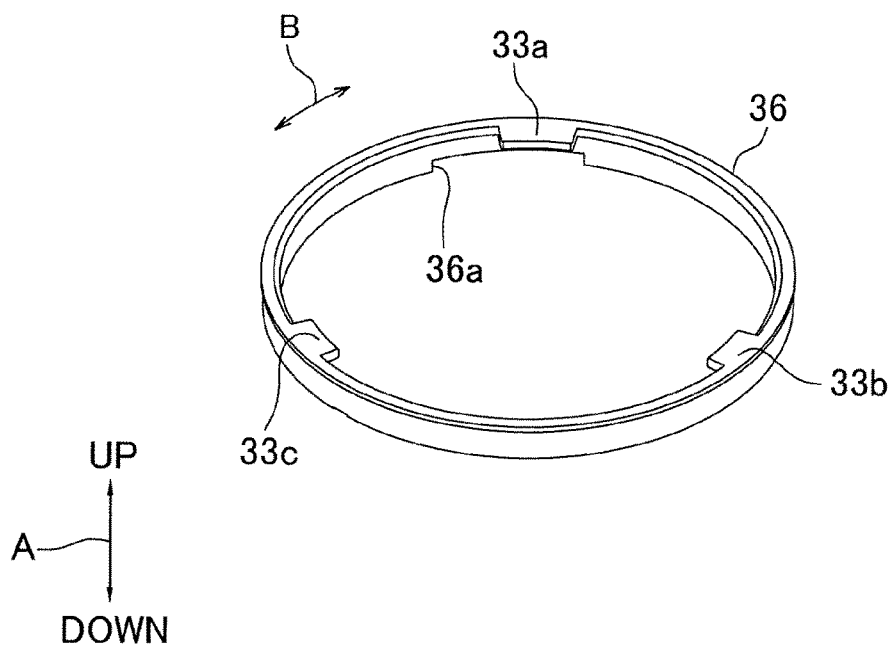
FIG. 6A is a perspective view of an annular portion shown in FIG. 5A.
Figure 6B:
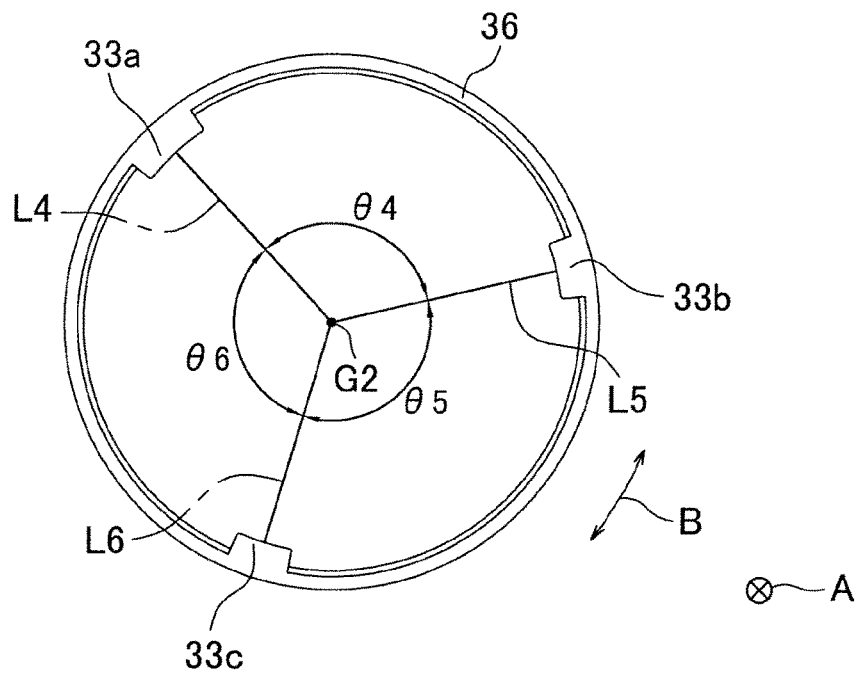
FIG. 6B is a plan view of the annular portion shown in FIG. 5A.

As shown in FIG. 6A and FIG. 6B, the annular portion 36 has an annular shape (circular ring shape). The height of the annular portion 36 in the up-down direction A is smaller than the width of the groove 31d. As shown in FIG. 3, FIG. 5A, and FIG. 5B, the annular portion 36 is provided in the groove 31d. The annular portion 36 has a recessed portion 36a passing through the annular portion 36 in the radial direction. The length of the recessed portion 36a in the extending direction B is longer than that of the first restricting portion 32, as shown in FIG. 5A and FIG. 5B. Specifically, the recessed portion 36a has a length such that the second restricting portions 33a to 33c do not come into contact with the first restricting portion 32 when moving from their first position to their second position. This will be detailed later.

The three second restricting portions 33a to 33c are provided between the first restricting portion 32 and the three opposed portions 31a to 31c with respect to the up-down direction A, so as to protrude inward from the inner circumferential surface of the annular portion 36. That is, the second restricting portions 33a to 33c are provided inward of the annular portion 36 and the collar portion 31. Furthermore, the three second restricting portions 33a to 33c are located above the flange 55 of the container 50 placed on the table portion 20, with respect to the up-down direction A. As shown in FIG. 6A and FIG. 6B, the three second restricting portions 33a to 33c are arranged apart from one another with respect to the extending direction B. Line segments connecting respective midpoints of the second restricting portions 33a to 33c in the extending direction B to a center G2 of the annular portion 36 are called line segments L4 to L6. As shown in FIG. 6B, angles θ4 to θ6 formed by the line segments L4 to L6 are equal to one another. As shown in FIG. 2A and FIG. 5A, the second restricting portion 33a is opposed to the opposed portion 31a in the up-down direction A, and corresponds to the recessed portion 56a. The second restricting portion 33b is opposed to the opposed portion 31b in the up-down direction A, and corresponds to the recessed portion 56b. The second restricting portion 33c is opposed to the opposed portion 31c in the up-down direction A, and corresponds to the recessed portion 56c. As shown in FIG. 5A, the length of the second restricting portion 33a in the extending direction B is shorter than the length of the first restricting portion 32 in the extending direction B. That is, the second restricting portion 33a is shorter than the recessed portion 56a. Furthermore, the second restricting portions 33b and 33c have the substantially same length in the extending direction B, which is shorter than the length of the opposed portion 31b in the extending direction B. That is, the second restricting portions 33b and 33c are shorter than the recessed portions 56b and 56c.

The three second restricting portions 33a to 33c are moved by the second moving mechanism 34 between the first position and the second position. The first position is the position in which the second restricting portions 33a to 33c are opposed to, in the up-down direction A, the flange 55 of the container 50 placed on the table portion 20, as shown in FIG. 7B. To be more specific, in the first position, a first end (in FIG. 7A and FIG. 7B, the right end) of the second restricting portion 33a in the extending direction B is opposed to the flange 55, and a second end of the second restricting portion 33a in the extending direction B is opposed to the recessed portion 56a and the first restricting portion 32 in the up-down direction A. Similarly to the above, when the second restricting portion 33b, 33c is in the first position, its first end in the extending direction B is opposed to the flange 55, while its second end in the extending direction B is opposed to the corresponding recessed portion 56b, 56c. Thus, in the first position, the second restricting portion 33a is opposed to and partially overlap the flange 55 and the recessed portion 56a. Due to this, if a gap exists between a first end (the right end in FIG. 7A and FIG. 7B) of the first restricting portion 32 in the extending direction B and the recessed portion 56a, foreign matter is less likely to enter the gap from above. This makes it easier to move the second restricting portion 33a from the first position to the second position. This improves reliability in lifting the movement restriction of the container 50 placed on the table portion 20. The second restricting portion 33b, 33c in the first position is also opposed to and partially overlap the flange 55 and the corresponding recessed portion 56b, 56c. Due to this, it is less likely that foreign matter enters, from above, a first end portion of the recessed portion 56b, 56c in the extending direction B. This also improves the reliability in lifting the movement restriction of the container 50 placed on the table portion 20, similarly to the above.

Figure 7A:
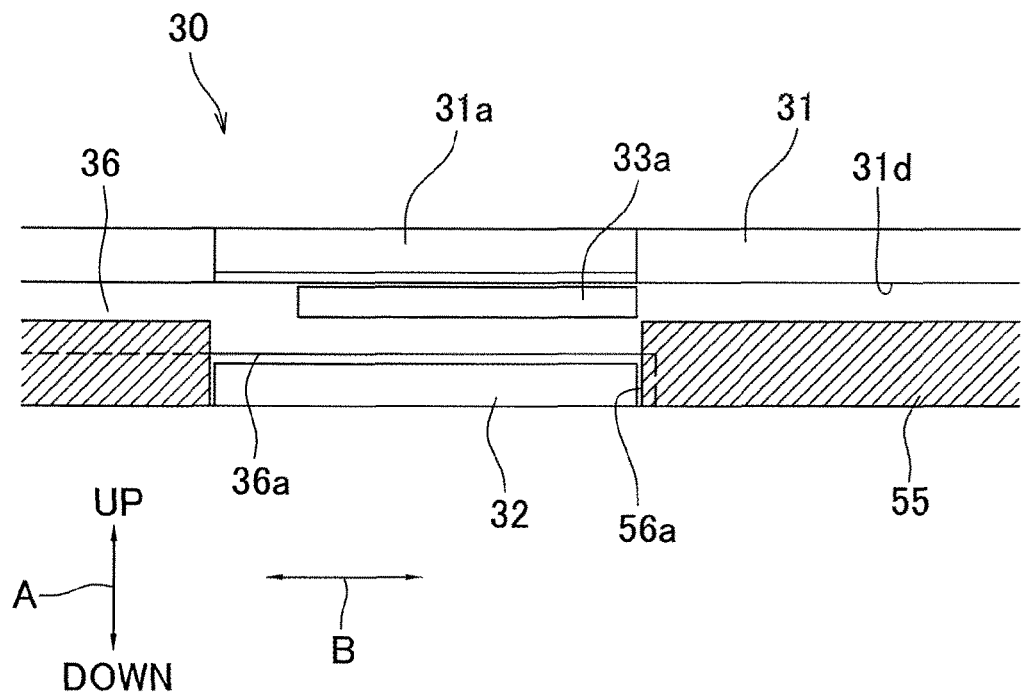
FIG. 7A is a cross section taken along a line VIIa-VIIa shown in FIG. 2A.
Figure 7B:
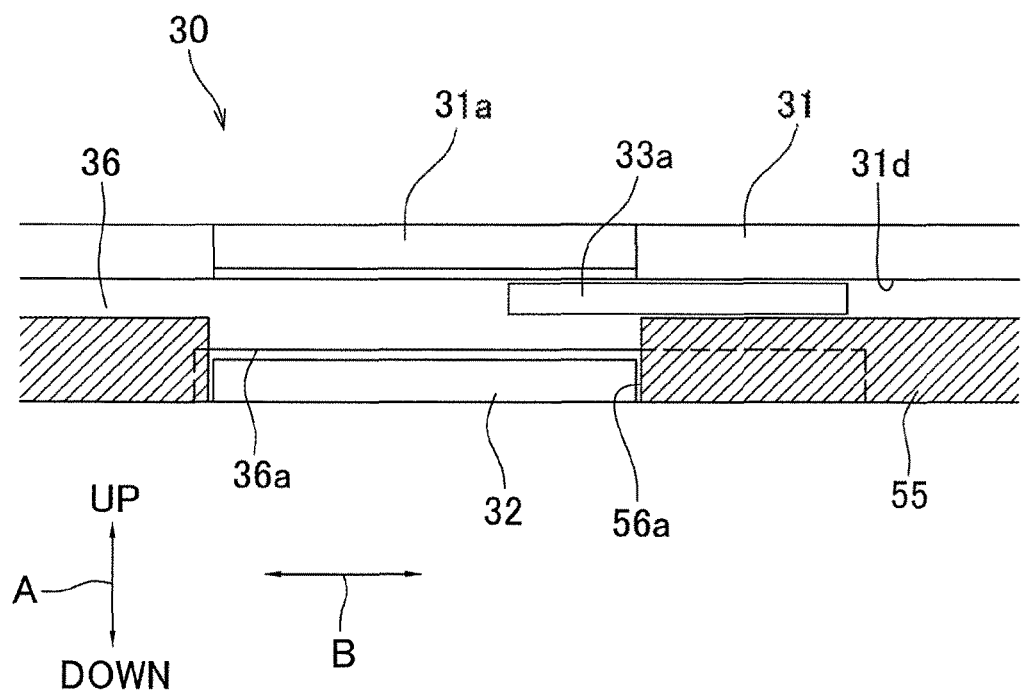
FIG. 7B is a cross section taken along a line VIIb-VIIb shown in FIG. 2B.

As shown in FIG. 7A, the second position is the position in which the second restricting portion 33a is opposed to the recessed portion 56a in the up-down direction A without being opposed to the flange 55 of the container 50 placed on the table portion 20. To be more specific, in the second position, the entirety of the second restricting portion 33a is opposed to the first restricting portion 32, and the first end of the second restricting portion 33a in the extending direction B is opposed to the first end of the first restricting portion 32. Because the second restricting portion 33a is shorter than the first restricting portion 32 in the extending direction B, the second end (the left end in FIG. 7A and FIG. 7B) of the second restricting portion 33a is relatively distant from the flange 55 when the second restricting portion 33a is in the second position. Due to this, even if foreign matter exists on the first restricting portion 32 and in the recessed portion 56a, it is relatively easier for the second restricting portion 33a to return from the first position to the second position. Furthermore, the above arrangement reduces the possibility that a finger of a user is caught between the second end of the second restricting portion 33a and the flange 55 when the second restricting portion 33a is moved from the first position to the second position. Similarly to the above, when the second restricting portion 33b, 33c is in the second position, the second restricting portion 33b. 33c is not opposed to the flange 55 in the up-down direction A, but the entirety of the second restricting portion 33b, 33c is opposed to the corresponding recessed portion 56b, 56c in the up-down direction A. To be more specific, in the second position, the first end of the second restricting portion 33b, 33c in the extending direction B is opposed to the first end of the corresponding recessed portion 56b, 56c. Due to this, advantageous effects similar to the above are provided.

The following will describe the operation of the content moving device 1. A sensor (not illustrated) configured to detect whether the container 50 is placed on the table portion 20 is provided to the main body case 10. Based on a detection signal from the sensor, the controller 100 controls the restricting mechanism 30 and the like. That is, when the container 50 containing therein the cassette 60 containing the cell culture plates 61 is placed on the table portion 20 and then a signal indicating that the container 50 has been placed is output from the sensor to the controller 100, the controller 100 controls the restricting mechanism 30, i.e., controls the drive motor 35, so as to rotate the annular portion 36. This moves the second restricting portions 33a to 33c from the second position to the first position along the extending direction B. As a result, it is possible to hold the container 50 on the main body case 10 while restricting the movement of the container 50 relative to the table portion 20 in the extending direction B, horizontal directions other than the extending direction B, and the up-down direction A.

The restricting mechanism 30 is configured so that the center of the container 50 substantially matches with the center of the collar portion 31 when the container 50 is placed on the table portion 20. Due to this, when the container 50 is placed on the table portion 20, the bottom lid 53 is placed on the up-down table 41 closing the communication hole 21, as shown in FIG. 3. Meanwhile, when the container 50 is not placed on the table portion 20, the up-down table 41 is positioned at the closed position in which the up-down table 41 closes the communication hole 21 and the second restricting portions 33a to 33c are positioned in the second position, under control of the controller 100. When the container 50 is placed on the table portion 20, the second restricting portions 33a to 33c have to be in the second position. If not, the flange 55 comes into contact with the second restricting portions 33a to 33c, and therefore the container 50 cannot be placed on the table portion 20.

Then, the controller 100 controls the camshaft driving mechanism so as to cause the locking/unlocking mechanism to transition from the locked state to the unlocked state. Thereafter, the controller 100 controls the up-down mechanism 42 so as to move the up-down table 41 from the closed position to the open position. At this time, the cassette 60 containing the cell culture plates 61 is moved to the internal space S with the bottom lid 53 on the up-down table 41. Subsequently, hydrogen peroxide gas is charged into the internal space S by the gas generator. In this way, the cell culture plates 61 are sterilized. Furthermore, at this time, the internal space S communicates with the space inside the container main body 51, and therefore the inner surface of the container main body 51 is also sterilized. In addition, the bottom lid 53 is sterilized as well because it is in the internal space S. After the sterilization is performed by the gas generator, the gas in the internal space S is replaced by clean air.

Subsequently, the controller 100 controls the up-down mechanism 42 and the camshaft driving mechanism so as to move the up-down table 41 from the open position to the closed position, and then so as to cause the locking/unlocking mechanism to transition from the unlocked state to the locked state. Thereafter, the controller 100 controls the drive motor 35 so as to rotate the annular portion 36, to move the second restricting portions 33a to 33c from the first position to the second position along the extending direction B. This allows the container 50, having the sterilized inside, cell culture plates 61, and cassette 60, to be detached from the main body case 10.

As described above, in the content moving device 1 of this embodiment, moving the second restricting portion 33a from the second position to the first position in the situation in which the container 50 is placed on the table portion 20 causes the second restricting portion 33a to be opposed to the flange 55 in the up-down direction A, and this restricts the movement of the container 50 in the up-down direction A. If foreign matter exists on the flange 55 of the container 50 and within the moving range of the second restricting portion 33a when restricting the movement of the container 50 placed on the table portion 20 as above, the second restricting portion 33a moves along the extending direction B of the flange 55, and therefore the second restricting portion 33a pushes the foreign matter aside to move from the second position to the first position. This reduces the possibility that foreign matter is caught between the second restricting portion 33a and the flange 55, and makes it easier to restrict the movement of the container 50 in the up-down direction A. As a result, reliability in the restriction of the movement of the container 50 is improved. Furthermore, because the first restricting portion 32 is provided, the movement of the container 50 is restricted with respect to the extending direction B of the flange 55, and foreign matter is less likely to enter the recessed portion 56a of the container 50 placed on the table portion 20.

The length of the second restricting portion 33a in the extending direction B is shorter than that of the first restricting portion 32, and the entirety of the second restricting portion 33a is opposed to the first restricting portion 32 in the up-down direction A when the second restricting portion 33a is in the second position. This makes it possible to reduce the length of the recessed portion 56a with respect to the extending direction B. Suppose that only a part of the second restricting portion 33a is opposed to the first restricting portion 32 in the up-down direction A when the second restricting portion 33a is in the second position. In this case, the length of the recessed portion 56a in the extending direction B has to be longer. However, in the present embodiment, the entirety of the second restricting portion 33a is opposed to the first restricting portion 32. This allows the recessed portion 56a to have a length shorter than the above case. This further reduces the range of the movement of the container 50 with respect to the extending direction B.

The restricting mechanism 30 includes the opposed portions 31a to 31c configured to be respectively opposed to the second restricting portions 33a to 33c in the up-down direction A. This reduces the possibility that a finger of a user or the like contacts any of the second restricting portions 33a to 33c when the second restricting portions 33a to 33c are moved.

The flange 55 is shaped to provide the plurality of recessed portions 56a to 56c, and the restricting mechanism 30 includes the second restricting portions 33a to 33c respectively corresponding to the recessed portions 56a to 56c. This makes it possible to more effectively restrict the movement of the container 50 placed on the table portion 20, with respect to the up-down direction A.

The flange 55 has an annular shape. As well, the collar portion 31 has an annular shape. The second moving mechanism 34 includes the drive motor 35, the annular portion 36, and the transmission mechanism 37. This makes it possible to move the second restricting portions 33a to 33c by the single drive motor 35 while achieving simplification of the structure of the second moving mechanism 34.

The table portion 20 has the communication hole 21, and the first moving mechanism 40 includes the up-down table 41 and the up-down mechanism 42. This makes the structure of the first moving mechanism 40 simple.

Figure 8A:
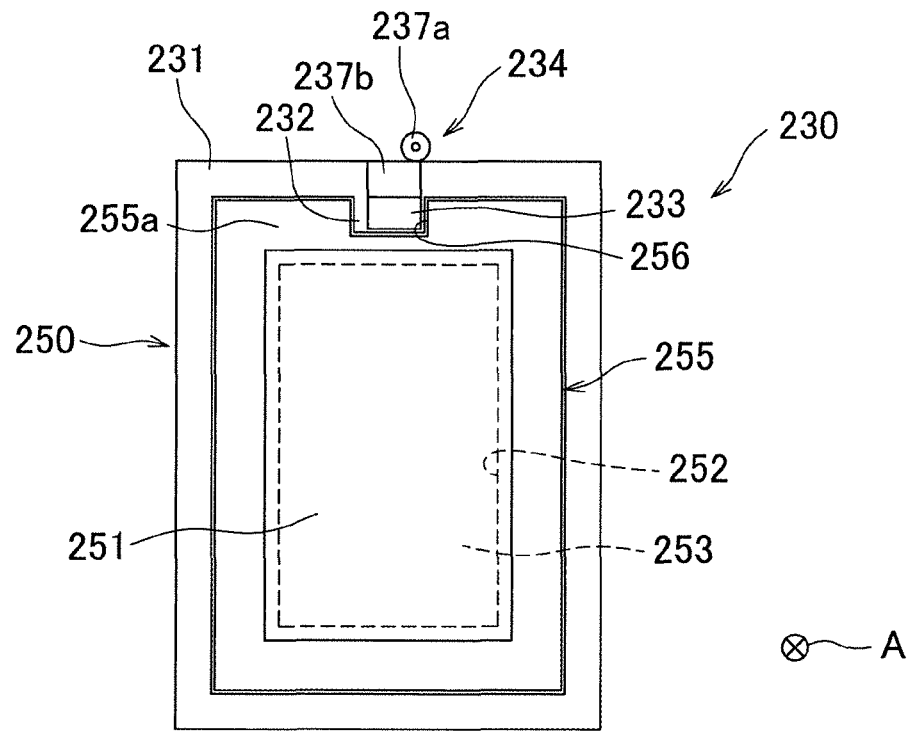
FIG. 8A is a plan view of a content moving device related to First Modification of the present invention, and illustrating the state in which the movement of a container is not restricted.
Figure 8B:
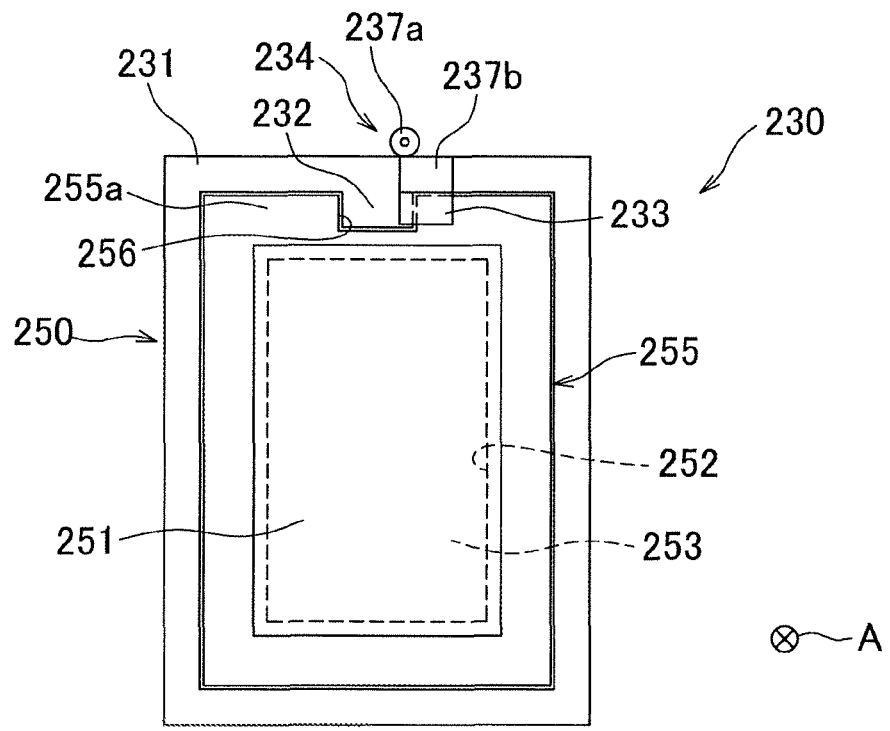
FIG. 8B is a plan view of the content moving device related to First Modification of the present invention, and illustrating the state in which the movement of the container is restricted.

In the embodiment described above, the container 50 has a circular planar shape, and the restricting mechanism 30 has an annular shape (circular ring shape) corresponding to the container 50. However, there may be the following variation: a container 250 and a restricting mechanism 230 both have a quadrangular planar shape, as shown in FIG. 8A and FIG. 8B. In this First Modification, the container 250 includes: a container main body 251 having a quadrangular planar shape; a flange 255 of a quadrangular ring shape provided around an opening 252 of the container main body 251; and a bottom lid 253 capable of hermetically closing the opening 252. A recessed portion 256 is provided at a side 255a of the flange 255, the side 255a extending in a left-right direction in FIG. 8A and FIG. 8B.

The restricting mechanism 230 includes: a collar portion 231 of a quadrangular ring shape; a first restricting portion 232; a second restricting portion 233; and a second moving mechanism 234. The first restricting portion 232 is provided so as to protrude inward from a part 231a of the collar portion 231 which corresponds to the side 255a. The first restricting portion 232 is shaped so as to be slightly smaller than the recessed portion 256, to allow the first restricting portion 232 to be located in the recessed portion 256 when the container 250 is placed on the table portion. The second restricting portion 233 is provided above the first restricting portion 232 with respect to the up-down direction A, and inward of the collar portion 231. The second restricting portion 233 is configured so that the entirety of thereof is opposed to the first restricting portion 232 when the second restricting portion 233 is in the second position. That is, the second restricting portion 233 is shaped so as to be smaller than the first restricting portion 232 and the recessed portion 256 with respect to the left-right direction.

The second moving mechanism 234 includes: a drive motor (not illustrated); a worm gear (not illustrated) provided to a rotation shaft of the drive motor, a pinion gear 237a meshing with the worm gear; and a rack gear 237b meshing with the pinion gear 237a. The rack gear 237b is provided so as to be movable along an extending direction in which the side 255a extends (i.e., in the left-right direction in FIG. 8A and FIG. 8B). The drive motor is driven and controlled by a controller. As the drive motor is driven, the rack gear 237b is moved along the left-right direction, via the worm gear and the pinion gear 237a. The rack gear 237b is fixed to the second restricting portion 233. That is, as the rack gear 237b moves along the left-right direction, the second restricting portion 233 also moves along the left-right direction.

The second restricting portion 233 is moved by the second moving mechanism 234 between the first position and the second position. The first position is the position in which the second restricting portion 233 is opposed to, in the up-down direction A, the flange 255 (the side 255a) of the container 250 placed on the table portion, as shown in FIG. 8B. To be more specific, in the first position, the right end of the second restricting portion 233 in the left-right direction is opposed to the flange 255, and the left end of the second restricting portion 233 in the left-right direction is opposed to the recessed portion 256 and the first restricting portion 232 in the up-down direction A. Thus, in the first position, the second restricting portion 233 is opposed to and partially overlap the flange 255 and the recessed portion 256. Due to this, advantageous effects similar to those of the above-described embodiment are provided.

As shown in FIG. 8A, the second position is the position in which the second restricting portion 233 is opposed to the recessed portion 256 in the up-down direction A without being opposed to the flange 255 of the container 250 placed on the table portion. To be more specific, in the second position, the entirety of the second restricting portion 233 is opposed to the first restricting portion 232, and the right end of the second restricting portion 233 in the left-right direction is opposed to an end of the first restricting portion 232. Because the second restricting portion 233 is shorter than the first restricting portion 232 in the left-right direction, the left end of the second restricting portion 233 is relatively distant from the flange 255 when the second restricting portion 233 is in the second position. Due to this, advantageous effects similar to those of the above-described embodiment are provided.

Also in the content moving device of First Modification, moving the second restricting portion 233 from the second position to the first position in the situation in which the container 250 is placed on the table portion causes the second restricting portion 233 to be opposed to the flange 255 in the up-down direction A, and this restricts the movement of the container 250 in the up-down direction A. If foreign matter exists on the flange 255 of the container 250 and within the moving range of the second restricting portion 233 when restricting the movement of the container 250 placed on the table portion as above, the second restricting portion 233 moves along the extending direction of the side 255a of the flange 255 (i.e., the left-right direction), and therefore the second restricting portion 233 pushes the foreign matter aside to move from the second position to the first position. This reduces the possibility that foreign matter is caught between the second restricting portion 233 and the flange 255, and makes it easier to restrict the movement of the container 250 in the up-down direction A. As a result, reliability in the restriction of the movement of the container 250 is improved. Furthermore, because the first restricting portion 232 is provided, the movement of the container 250 is restricted with respect to the left-right direction of the flange 255, and foreign matter is less likely to enter the recessed portion 256 of the container 250 placed on the table portion.

Figure 9:
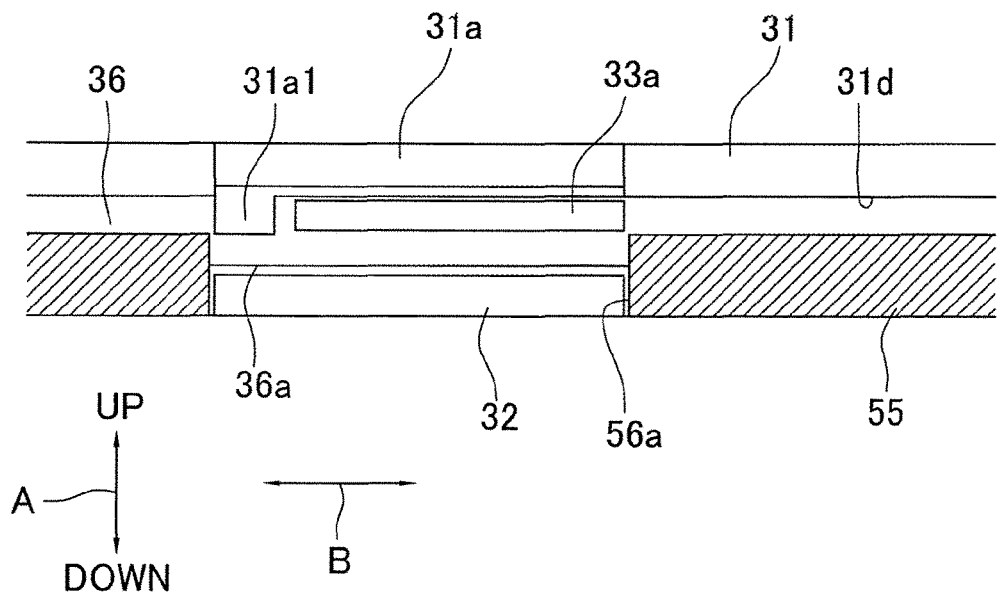
FIG. 9 is a diagram illustrating an opposed portion of a content moving device related to Second Modification of the present invention.

Second Modification as below is also possible. In Second Modification, as shown in FIG. 9, a protrusion 31a protruding downward is provided at a left end of the opposed portion 31a. The protrusion 31a1 is configured so as to be opposed to the second restricting portion 33a in the extending direction B, not in the up-down direction A, when the second restricting portion 33a is in the second position. This further makes it less likely that foreign matter or the like enters the recessed portion 56a of the container 50 placed on the table portion 20.

Figure 10:
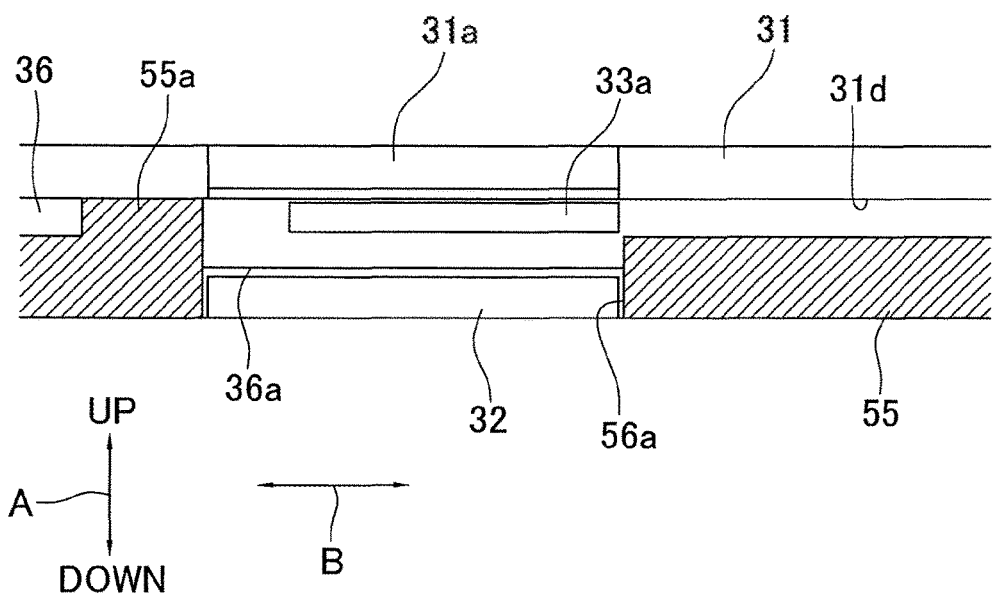
FIG. 10 is a diagram illustrating a modification of a flange of the container.

As shown in FIG. 10, a protrusion 55a protruding upward may be provided at a part of the flange 55, the part being adjacent to the left end of the recessed portion 56a. This further makes it less likely that foreign matter or the like enters the recessed portion 56a of the container 50 placed on the table portion 20.

A preferred embodiment of the present invention has been described. It should be noted that the present invention is not limited to the above-described embodiment, and various changes, substitutions, and alterations can be made herein without departing from the spirit and scope of the invention as defined by the appended claims. While the content moving device in the embodiment and modifications described above is configured so that gas is charged into the internal space S, gas charging is not essential. That is, it is only required for the content moving device to be capable of moving its content from the container 50, 250 to the internal space S.

While in the above-described embodiment the three second restricting portions 33a to 33c are provided, the number of second restricting portions may be one, two, or four or more. The number of second restricting portions is changeable as long as recessed portion(s) of the same number as that of second restricting portions are provided to the flange of the container. The thickness of the first restricting portion 32 in the up-down direction A may be equal to the thickness of the flange 55. The length of the second restricting portion 33a in the extending direction B may be equal to that of the first restricting portion 32 as long as it is shorter than that of the recessed portion 56a.

In the above-described embodiment, when the second restricting portion 33a is in the second position, the entirety of the second restricting portion 33a is opposed to the first restricting portion 32 in the up-down direction A. However, the second restricting portion 33a may be provided so as to be partially opposed to, or so as not to be opposed to the first restricting portion 32 when the second restricting portion 33a in the second position, as long as the entirety of the second restricting portion 33a is opposed to the recessed portion 56a in the up-down direction A. Furthermore, in the first position, the second restricting portion 33a may be opposed to the flange 55 in the up-down direction A without being opposed to the recessed portion 56a in the up-down direction A. Furthermore, the collar portion 31 does not have to have the opposed portions 31a to 31c. Still further, a driving source other than the drive motor 35 may be used.

REFERENCE SIGNS LIST

1: content moving device
10: main body case
20: table portion
21: communication hole
30: restricting mechanism
31, 231: collar portion
31a-31c: opposed portion
32, 232: first restricting portion
33a-33c, 233: second restricting portion
34, 234: second moving mechanism
35: drive motor (driving source)
36: annular portion
37: transmission mechanism
40: first moving mechanism
41: up-down table
42: up-down mechanism
50, 250: container
51, 251: container main body
52, 252: opening
53, 253: bottom lid
55, 255: flange
56a-56c: recessed portion
61: cell culture plate (content)

The invention claimed is:
1. A content moving device configured to allow a container to be placed thereon, the container including: a container main body capable of containing content and having an opening which opens downward; a bottom lid capable of hermetically closing the opening; and a flange provided around the opening and shaped to provide at least one recessed portion, the content moving device comprising:
 a main body case having an internal space;
 a table portion provided on an upper wall of the main body case and configured to allow the container to be hermetically placed on the table portion;
 a restricting mechanism configured to restrict movement of the container placed on the table portion; and
 a first moving mechanism configured to move the content to the internal space with the bottom lid of the container restricted by the restricting mechanism, wherein
 the restricting mechanism includes:
 a collar portion provided on the table portion in a standing manner and configured to surround the flange of the container placed on the table portion;

a first restricting portion provided inward of the collar portion and configured to be located in the recessed portion when the container is placed on the table portion;

at least, one second restricting portion shorter than the recessed portion with respect to an extending direction of the flange in which the flange extends, the second restricting portion being provided above the first restricting portion and inward of the collar portion; and a second moving mechanism configured to move the second restricting portion along the extending direction between a first position, in which the second restricting portion is opposed to the flange of the container placed on the table portion in an up-down direction, and a second position, in which the second restricting portion is opposed to the recessed portion in the up-down direction without being opposed to the flange in the up-down direction.

2. The content moving device according to claim 1, wherein a length of the second restricting portion in the extending direction is equal to or shorter than that of the first restricting portion, and an entirety of the second restricting portion is opposed to the first restricting portion in the up-down direction when the second restricting portion is in the second position.

3. The content moving device according to claim 2, wherein when the second restricting portion is in the first position, a first end of the second restricting portion in the extending direction is opposed to the flange in the up-down direction and a second end of the second restricting portion in the extending direction is opposed to the first restricting portion in the up-down direction.

4. The content moving device according to claim 3, wherein the restricting mechanism further includes at least one opposed portion provided above the second restricting portion so as to protrude inward from the collar portion, the opposed portion being configured to be opposed to the second restricting portion in the up-down direction when the second restricting portion is in the second position.

5. The content moving device according to claim 4, wherein the restricting mechanism includes a plurality of the second restricting portions provided apart from one another along the extending direction and respectively corresponding to a plurality of the recessed portions.

6. The content moving device according to claim 5, wherein the restricting mechanism includes a plurality of the opposed portions configured to be respectively opposed to the second restricting portions in the up-down direction.

7. The content moving device according to claim 5,
wherein the collar portion has an annular shape, and
wherein the second moving mechanism includes: a driving source; an annular portion provided inward of the collar portion and provided with the second restricting portions on an inner circumferential surface of the annular portion; and a transmission mechanism configured to transmit driving force from the driving source to the annular portion so as to rotate the annular portion.

* * * * *